(12) United States Patent
Breindel et al.

(10) Patent No.: US 7,837,774 B2
(45) Date of Patent: Nov. 23, 2010

(54) BIOCIDE COMPOSITIONS FOR USE IN COATINGS

(75) Inventors: Kenneth Breindel, Lansdale, PA (US); Shailesh Shah, Dresher, PA (US); Ayaz A. Khan, Upper Darby, PA (US)

(73) Assignee: Cognis IP Management GmbH, Duesseldorf (DE)

( * ) Notice: Subject to any disclaimer, the term of this patent is extended or adjusted under 35 U.S.C. 154(b) by 40 days.

(21) Appl. No.: 12/331,932

(22) Filed: Dec. 10, 2008

(65) Prior Publication Data

US 2009/0145327 A1 Jun. 11, 2009

Related U.S. Application Data

(60) Provisional application No. 61/012,515, filed on Dec. 10, 2007.

(51) Int. Cl.
*A01N 33/00* (2006.01)
*A01N 29/00* (2006.01)

(52) U.S. Cl. ............... 106/18.32; 106/18.35; 424/405; 514/741; 558/411; 558/425; 570/182

(58) Field of Classification Search .............. 106/18.32, 106/18.35; 424/405; 514/741; 558/411, 558/425; 570/182
See application file for complete search history.

(56) References Cited

U.S. PATENT DOCUMENTS

| | | | | |
|---|---|---|---|---|
| 5,667,795 A | * | 9/1997 | Fraley et al. | 424/405 |
| 6,409,809 B1 | | 6/2002 | Breindel et al. | 106/18.32 |
| 7,316,738 B2 | * | 1/2008 | Richardson et al. | 106/18.32 |
| 2005/0255251 A1 | * | 11/2005 | Hodge et al. | 427/397 |
| 2007/0131136 A1 | * | 6/2007 | Zhang et al. | 106/15.05 |

FOREIGN PATENT DOCUMENTS

WO  WO2005/110692 A2 * 11/2005

\* cited by examiner

*Primary Examiner*—Anthony J Green

(57) ABSTRACT

Biocide compositions capable of increasing the fading resistance of a coating material, which compositions preferably comprise a nano-sized halogenated benzonitrile and a nano-sized zinc oxide, are disclosed. Coating compositions, which comprise the biocide compositions, binders, and pigments are disclosed. The biocide compositions are particularly suitable for use in paints. Methods for reducing the fading of pigmented coating compositions upon exposure to light are also disclosed.

3 Claims, No Drawings

BIOCIDE COMPOSITIONS FOR USE IN COATINGS

CROSS-REFERENCE TO RELATED APPLICATIONS

This application claims priority under 35 U.S.C. Section 119 of U.S. Provisional Application No. 61/012,515 filed Dec. 10, 2007, the entire contents of which are incorporated herein by reference.

BACKGROUND OF THE INVENTION

Biocides have been useful in various coating and paint formulations, such as house paints, to prevent the growth of microorganisms such as bacteria, mold, and mildew. However, certain biocides can undergo undesirable photochemical reactions upon exposure to ultraviolet (UV) radiation. This poses a problem especially for water-based exterior house paints, which are exposed to sunlight.

Halogenated benzonitrile-based biocides, such as chlorothalonil, are effective at suppressing the growth of fungi, but, when used in paints, present a problem of fading of colored paints upon exposure to UV radiation. The fading is believed to be related to degradation of the binder, which produces chalking. Although the chalking can occur in light as well as dark colored paints, it is especially noticeable with dark or deeply hued pigments such as blacks and blues. This problem precludes the use of halogenated benzonitrile based-biocides in such paints.

U.S. Pat. No. 6,409,809 describes a coating composition of a halogenated benzonitrile, such as chlorothalonil, in combination with a conazole compound. While effective at reducing the fading of colored paints, the coating compositions described therein are economically prohibitive to make and sell to the consumer.

There thus remains a need to provide a biocide composition of a halogenated benzonitrile, such as chlorothalonil, for use in coating materials, such as paints, which composition will effectively address the problem of fading of colored paints upon exposure to light, without significantly raising the costs of such paints to the consumer.

SUMMARY OF THE INVENTION

One aspect of the present invention addresses the above-described need by providing a biocide composition for increasing the fading resistance of a coating material, which composition preferably comprises a nano-sized halogenated benzonitrile and a nano-sized zinc oxide.

The biocide compositions of the invention are particularly suitable for use in paints.

Another aspect then of the present invention is a coating composition which comprises the biocide composition of the invention, a binder, and a pigment.

Another embodiment of the present invention is directed to a method for reducing the fading of pigmented coating compositions, which method comprises:

1) providing a pigmented composition containing an amount of pigment sufficient to provide a coating composition having a reflectance of no more than about 25%; and
2) adding to the pigmented composition, a biocide composition effective for increasing the fading resistance of a coating material, which composition comprises a nano-sized halogenated benzonitrile and a nano-sized zinc oxide.

DETAILED DESCRIPTION OF THE PREFERRED EMBODIMENTS

The present invention provides biocide compositions for increasing the fading resistance of a coating material, which compositions preferably comprise a nano-sized halogenated benzonitrile and a nano-sized zinc oxide.

Halogenated benzonitriles are described in U.S. Pat. No. 6,409,809, which is incorporated herein by reference in its entirety.

A particularly preferred halogenated benzonitrile is tetrachloroisophthalonitrile, more commonly known as chlorothalonil (or "CTL").

Chlorothalonil can be provided, for example, in a dispersant and milled to the desired nano-sized dispersion. NOPCOCIDE® N40D from Cognis Corporation is a non-limiting example of a suitable source of a chlorothalonil dispersion suitable for use in the present invention.

While not limited by or bound to any particular theory, nano-sized chlorothalonil particles are believed to exhibit improved efficacy due, at least in part, to an increased surface area, making the particles essentially invisible so that the composition of the invention can be used in clear coatings without causing haze.

To the nano-sized chlorothalonil is preferably added a nano-sized zinc oxide, which essentially is opaque to UV light, to provide the preferred compositions of the invention. The nano-sized zinc oxide can further enhance the biocidal efficacy of the composition, while further advantageously protecting chlorothalonil from UV light, which exposure results in chalking and fading of dark colors.

A non-limiting example of a suitable source of nano-sized zinc oxide is DECELOX® available from Elementis Pigments.

It shall be understood that the invention encompasses embodiments where the chlorothalonil and zinc oxide are milled to the desired nano-sized particles separately and then added together, or are first added together and then milled to the desired nano-sized particles.

Nano particles of chlorothalonil and zinc oxide preferably range from about 10 nm to about 300 nm, with about 10 nm to about 100 nm being preferred.

The ratios of widely, but in preferred embodiments, are chlorothalonil to zinc oxide in the biocide composition of the invention can range from about 1:20 to about 10:1.

The preferred compositions remain clear and retain UV/fading and chalking protection, while also exhibiting enhanced biocidal activity, especially fungicidal activity.

While the invention described herein may be used in conjunction with any type of coating material, it is especially suitable for use in paints. In particular, preferred aspects of the invention are especially useful for dark colored exterior paints, such as used on houses. As used herein, the term "dark" shall refer to coatings having a reflectance of no more than about 25%.

The biocide compositions of the invention are also suitable for use in clear exterior wood coatings, such as used on decks and the like. The preferred compositions can protect the wood from mildew as well as fading, while preserving the clarity of the coating. In the case of a pigmented stain, fading and chalking can be prevented by the UV-screening effect of the preferred nano-zinc oxide.

Another embodiment then of the present invention is a coating composition which comprises the biocide composition of the invention, a binder, and a pigment.

A paint is a coating material, which includes a solid pigment suspended in a liquid vehicle, and which is intended for application to various surfaces. The pigment can be inorganic or organic. Inorganic pigments can be white or colored and can include, for example, titanium oxide, zinc oxide, chromium oxide, iron oxide, carbon black, and various combinations thereof. Organic pigments can include, for example, para-chlorinated nitroanilines, naphthol red, Hansa, benzidine, dinitroaniline orange, lithol, Persian orange, tartrazine, alizarine, indathrene, indigo blue, indigo maroon, phthalocyanine blue, phthalocyanine green, rhodamine, malachite green, methyl violet, and Victoria blue.

The vehicle typically includes a binder and, usually, a solvent or diluent such as water, mineral spirits, alcohols, ethers, ketones and esters. Various binders are known and commonly used such as alkyds, acrylics, vinyls, latex, and combinations thereof. Latex or emulsion paints typically use water as the diluent. The paint dries after application to the surface by evaporation of the diluent and/or hardening of the binder by chemical reaction. Other components may optionally also be incorporated into the paint formulations such as dispersants, defoamers, surfactants, driers, extenders, and the like.

The preferred coating compositions of the invention include, in addition to the pigment, binder, and other optional components, the biocide compositions of the invention comprising from about 1% to about 99% by weight of a nano-sized halogenated benzonitrile compound and from about 1% to about 99% by weight of a nano-sized zinc oxide, preferably from about 10% to about 90% by weight of the halogenated benzonitrile compound and from about 10% to about 90% by weight of the zinc oxide, more preferably from about 20% to about 80% of the halogenated benzonitrile compound and from about 20% to about 80% of the zinc oxide, and most preferably about 40% to 60% of the halogenated benzonitrile compound and about 40% to 60% of the zinc oxide.

A particularly preferred halogenated benzonitrile is tetrachloroisophthalonitrile, more commonly known as chlorothalonil (or "CTL").

The nano-sized chlorothalonil and zinc oxide can be added to the coating composition as a ready-to-use blend or added separately.

When added to the coating composition separately, the nano-sized zinc oxide can be provided in an aqueous dispersant medium, which contains suitable pigment dispersants, such as HYDROPALAT®, a hydrophilic polyacrylate dispersant available from Cognis Corporation. Alternatively, the zinc oxide can be provided in an organic medium containing a dispersant such as polyglycol or an alkoxylated fatty alcohol, as non-limiting examples.

The biocide compositions described herein are preferably used in water-based acrylic paints. An exemplary composition for such paint is described below.

As used herein the term "acrylic" encompasses homopolymers and copolymers having unsubstituted or substituted acrylic moieties including acrylates, methacrylates, vinylacrylics, and styrenated acrylics.

More particularly, the pigment of the paint composition preferably includes particles of organic or inorganic pigment, the various types of which are well-known in the art and examples of which have been set forth above. A suitable pigment includes titanium oxide ($TiO_2$) such as Ti-Pure® R-960 brand titania available from DuPont. Also useful are extenders such as Gold Bond® R brand silica ($SiO_2$), available from Gold Bond. Moreover, various colorants can be added to provide different hues to the pigment. Such colorants are known in the art.

Acrylic binder can be provided in the form of an acrylic emulsion such as Rhoplex® AC-264 acrylic emulsion, available from Rohm & Haas Corp.

Desirable additives include primary pigment dispersants (e.g., NOPCOSPERSE®100 brand anionic polyelectrolyte, available from Cognis Corporation), co-dispersants (e.g., TRITON® CF-10 brand surfactant, available from Union Carbide), defoaming agents (e.g., FOAMASTER® VL defoamer, available from Cognis Corporation), antifreeze agents (e.g., ethylene glycol, propylene glycol), thickeners (e.g., NATROSOL® MHR brand hydroxyethyl cellulose, available from Hercules), rheology modifiers (e.g., ATTAGEL® 50 brand clay, available from Englehart Co.), coalescing agents (e.g., TEXANOL® brand high molecular weight alcohol type coalescing agent, available from Eastman Chemicals), and bactericides (e.g., NUOSEPT® 95 brand in-can preservative, available from Huls-Degussa).

A particularly preferred primary pigment dispersant is HYDROPALAT® hydrophilic polyacrylate, available from Cognis Corporation.

The following prophetic example is provided for the purpose of illustrating, but not necessarily limiting the scope of the present invention.

EXAMPLE

A paint composition is made by mixing the following ingredients in the following order:

| | |
|---|---|
| Deionized water | 450.0 parts by weight |
| NOPCOSPERSE ®100 (25%) | 18.0 parts by weight |
| TRITON ® CF-10 | 7.2 parts by weight |
| Ethylene glycol | 126.0 parts by weight |
| FOAMASTER ® VL | 3.6 parts by weight |
| NATROSOL ® MHR (2.5%) | 180.0 parts by weight (mix for 5 minutes) |
| TIPURE ® R-960 | 52.6 parts by weight |
| GOLD BOND ® silica | 1256.8 parts by weight (ground for 5 minutes) |
| ATTAGEL ® 50 | 6.0 parts by weight (add slowly and ground for 10-15 minutes) |
| RHOPLEX ® AC-264 | 1401.5 parts by weight |
| FOAMASTER ® VL | 10.8 parts by weight |
| TEXANOL ® | 10.8 parts by weight |
| NUOSEPT ® | 1.6 parts by weight |
| NATROSOL ® 250 MH2 (2.5%) | 361.8 parts by weight |

To the above composition is then added Huls COLORTREND® 'E' phthalocyanine blue colorant dispersion to an amount of about 12.5% by weight of the total paint composition.

An exposure test is conducted in two studies to determine the effect of weathering (UV exposure and/or condensation) on samples of panels with paints containing nano-sized chlorothalonil alone, nano-sized zinc oxide alone, and a blend of the two, respectively.

The blend is composed of nano-milled NOPCODIDE® N-40-D chlorothalonil diluted to 20% chorothalonil actives and 20% by weight of DECELOX® zinc oxide containing HYDROPALAT® 44.

The panels are aluminum having a 3003 alloy mill finish. One coating (6 mils thick when wet) of the selected paint is applied to each panel and allowed to air dry for 7 days at ambient temperature.

Simulated weathering is performed by exposure of the panels to a QUV accelerated weathering tester providing UVA radiation at a power consumption of 1200 Watts (110 volts, 60 Hz). The exposure is conducted in alternating and repeating 6-hour cycles, one 6-hour cycle being an ultraviolet radiation exposure cycle (conducted at 80° C.), and the other cycle being a condensation cycle wherein the panels are exposed to moisture (conducted at 60° C.).

By way of preferred aspects of the present invention, it is thus contemplated that biocide compositions of a halogenated benzonitrile, such as chlorothalonil, for use in coating materials, such as paints, are provided, which compositions will effectively address the problem of fading of colored paints upon exposure to light, without significantly raising the costs of such paints to the consumer.

We claim:

1. A method for reducing the fading of pigmented coating compositions, which method comprises:
    a) providing a pigmented composition containing an amount of pigment sufficient to provide a pigmented composition having a reflectance of no more than about 25%; and
    b) adding to said pigmented composition, an effective amount of a biocide composition effective for increasing the fading resistance of a coating material, which composition comprises a nano-sized halogenated benzonitrile and a nano-sized zinc oxide, in a ratio of about 1:20 to about 10:1,
    wherein the particle sizes of said halogenated benzonitrile and said zinc oxide range from about 10 nm to about 300 nm.

2. The method of claim 1 wherein said halogenated benzonitrile comprises chlorothalonil.

3. The method of claim 2 wherein said chlorothalonil is present in an amount of from about 20% to about 80% by weight and said zinc oxide is present in an amount of about 20% to about 80% by weight, based on the weight of said biocide composition.

* * * * *